Figure 1:
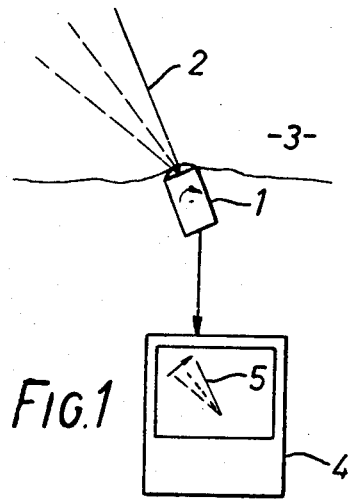

United States Patent [19]

Cole

[11] 4,232,556
[45] Nov. 11, 1980

[54] MOVING TRANSDUCER SYSTEMS

[75] Inventor: Allan Cole, Lasswade, Scotland

[73] Assignee: E M I Limited, Hayes, England

[21] Appl. No.: 16,496

[22] Filed: Mar. 1, 1979

[30] Foreign Application Priority Data

Mar. 7, 1978 [GB] United Kingdom ............... 8915/78

[51] Int. Cl.³ ............................................. G01N 29/04
[52] U.S. Cl. ........................................ 73/626; 73/628
[58] Field of Search ................ 73/625, 626, 628, 629, 73/639, 1 R; 128/660, 661; 367/104, 120

[56] References Cited

U.S. PATENT DOCUMENTS 3,779,234  12/1973  Eggleton et al. .................... 128/660

OTHER PUBLICATIONS

"Ultrasonic Visualization of Left Ventricular Dynamics", from IEEE Transactions on Sonics and Ultrasonics, Jul. 1970.

Primary Examiner—James J. Gill
Attorney, Agent, or Firm—Fleit & Jacobson

[57] ABSTRACT

In an ultrasonic transducer probe having multiple rotating transducer elements the transducer outputs are switched in response to sine and cosine signals from a resolver. The same signals are used to switch and time the display scan. If the transducers are misaligned a multiple blurred image may result. It is proposed to modify the resolver signals changing the phase of the signals for at least one transducer to bring the display signals into registration. In one example it is achieved by, for at least one transducer element output, mixing a proportion of at least one of the sine and cosine signals with the other.

20 Claims, 9 Drawing Figures

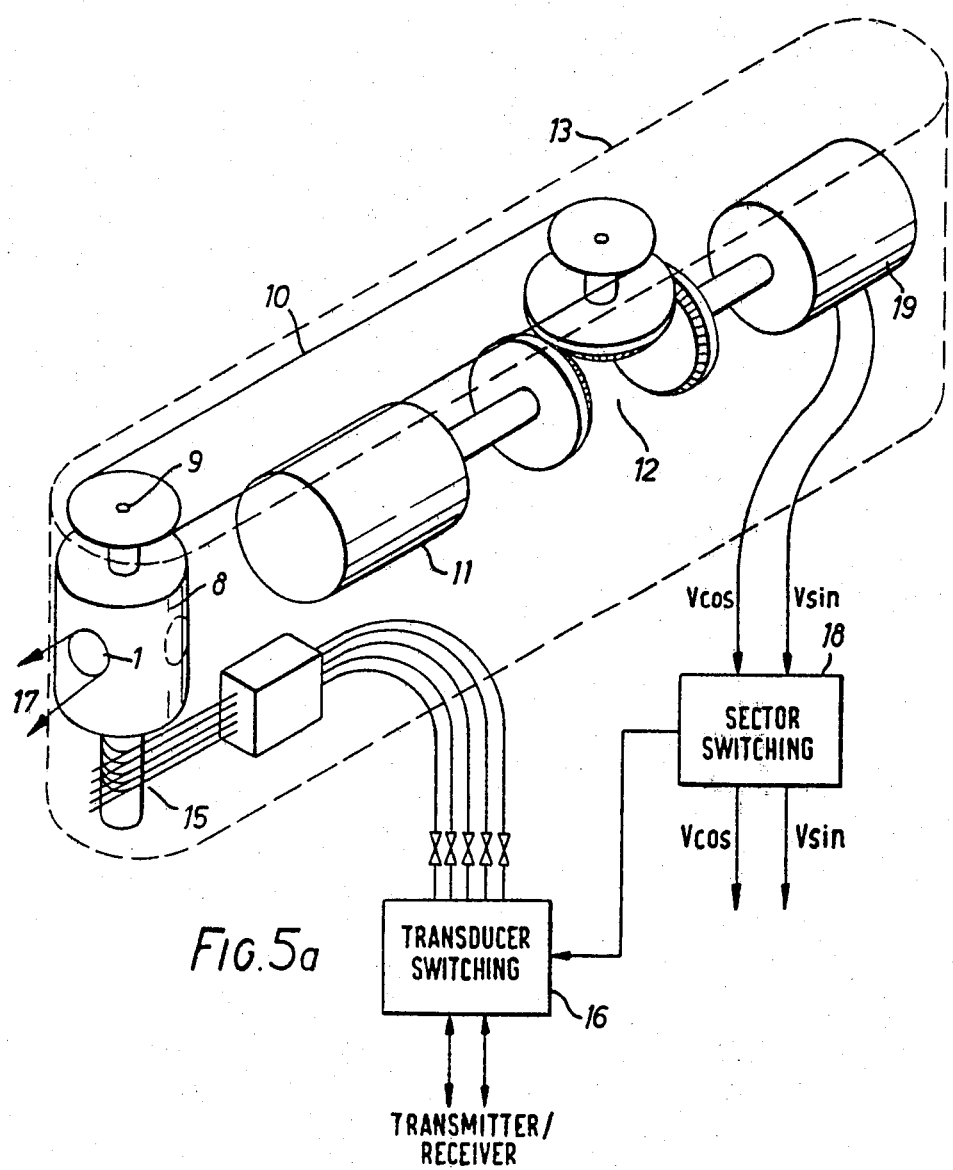

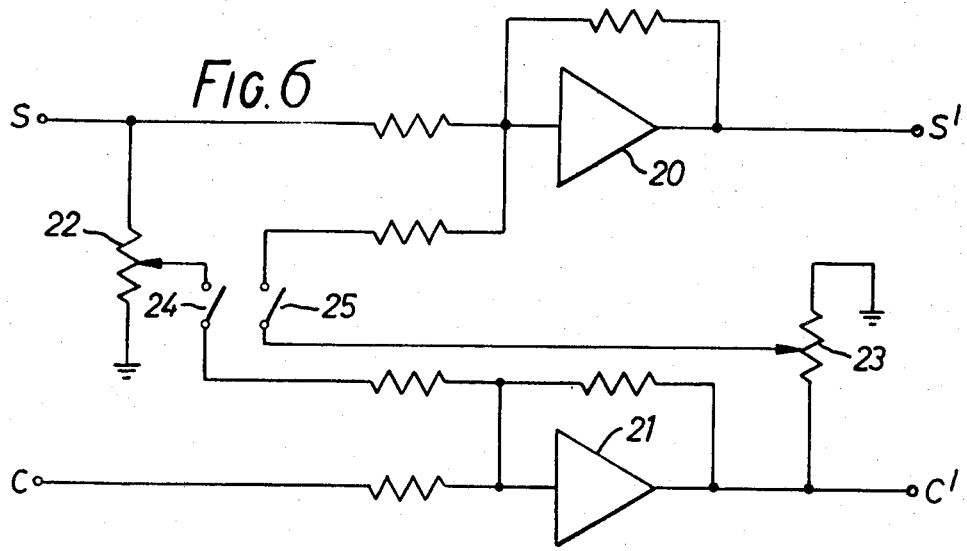
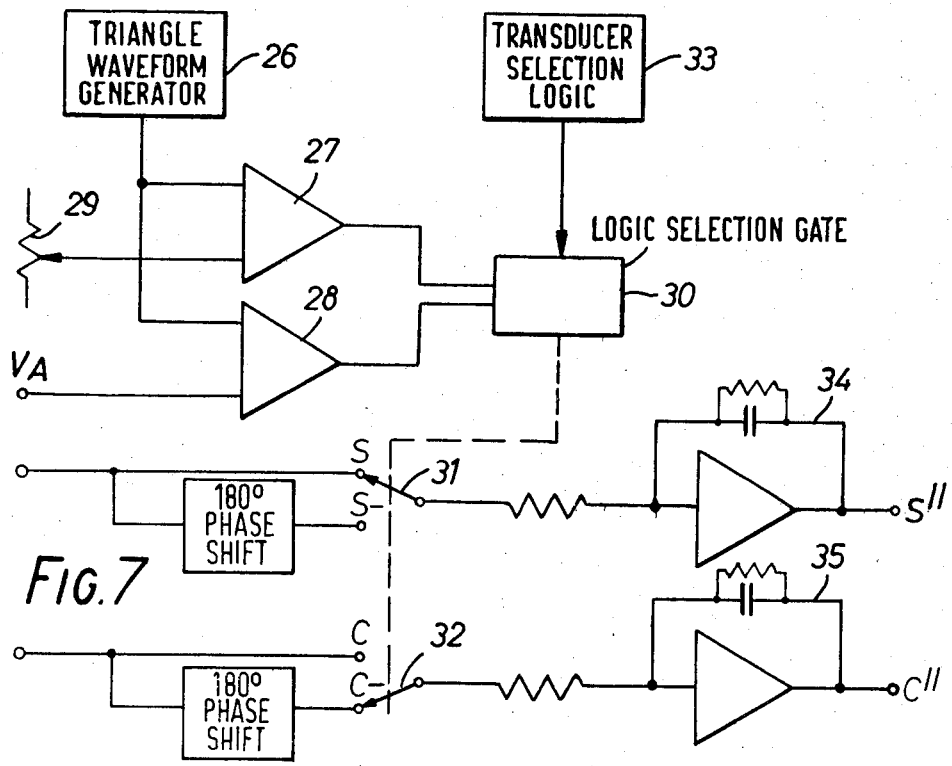

MOVING TRANSDUCER SYSTEMS

The present invention relates to transducer systems using two or more moving transducers, which produce individual outputs for co-ordination with each other. It is particularly, though not exclusively related to ultrasonic examination systems using two or more rotating transducers.

For ultrasonic examination, ultrasonic transmitting and receiving transducers can project a beam of energy into a body being examined and receive and display echoes received from objects or features disposed in the beam. It is also the practice to scan the transducers and hence the beam of ultrasonic energy in relation to the body, to receive echoes from a larger examined region. This may be achieved by rotating the transducer about a suitable axis. The transducer may be oscillated about this axis to continue to supply echo data, but it is convenient to rotate through 360° so that a new scan commences when the transducer is rotated back to the starting position. That arrangement has, however, a long 'dead' time in which the transducer points away from the body, and to fill this 'dead' time, it has been proposed to use one or more additional transducers. If the extra transducer(s) are accurately positioned, then successive scans start after equal time intervals. The display scan can then by synchronized with the transducer scan so that each successive scan overlies the others on display and fixed reflecting objects are displayed in the same place. This, however, requires high mechanical tolerances, and if they are not achieved, the displays may not superimpose.

It is an object of the invention to provide an arrangement for correcting or reducing such errors.

According to the invention, there is provided an arrangement for operating on sine and cosine components of a vector signal, representing at different times the positions of different ones of two or more moving investigative transducers, for control of a display on which the tranducer outputs are displayed in alternation, the arrangement including means for changing the phase of the vector signal when representing at least one of said transducers respective to the vector signal when representing a first transducer, to correct display errors resulting from misalignment of said at least one transducer relative to said first transducer.

According to another aspect of the invention, there is provided an ultrasonic examination system including: a probe unit which includes at least two transducers for alternately scanning a body to be examined; means for applying to a common display arrangement the output of the transducer currently scanning the body to display the outputs in alternation; means for providing sine and cosine components of a vector signal, representing the position within its scan of the transducer currently scanning, for control of the display of the respective output; means for modifying at least one component of the vector signal for at least one transducer to change the phase of the respective vector signal so that the alternating displays are maintained in the correct relative phase.

Figure 2:
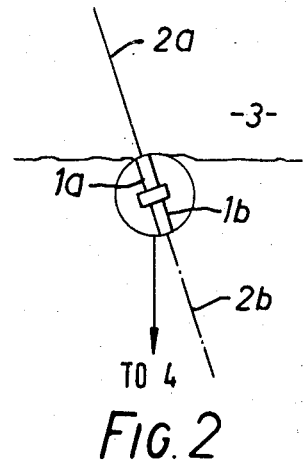
Figure 3:
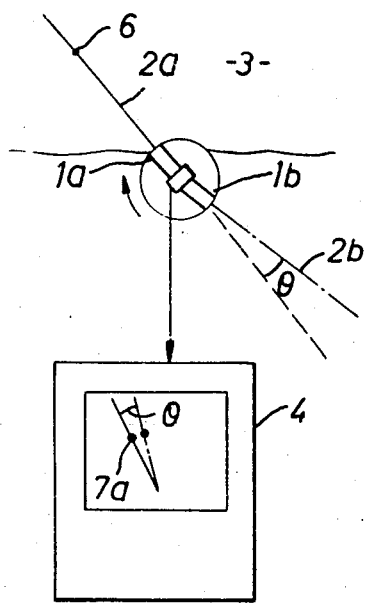
Figure 4A:
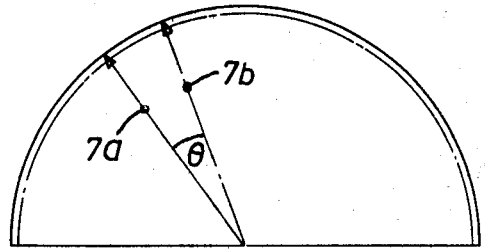
Figure 4B:
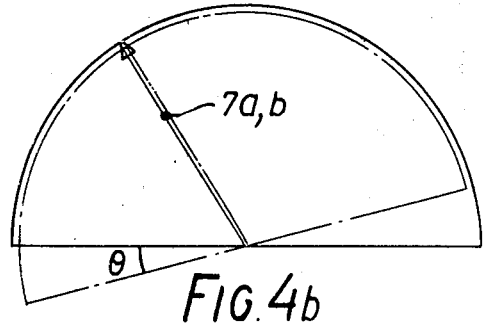

In order that the invention may be clearly understood and readily carried into effect, it will now be described by way of example with reference to the accompanying drawings, of which, FIG. 1 illustrates the basic operation of a rotating probe ultrasonic system, FIG. 2 shows a double probe system with which position errors may occur, FIG. 3 illustrates the cause of the transducer position errors, FIGS. 4a and 4b show in principle how the errors may be corrected, FIG. 5a and 5b show a practical ultrasonic probe in which the invention is incorporated, FIG. 6 shows one circuit for implementing the correction of the invention, and FIG. 7 shows an alternative circuit suitable for remote control.

A simple ultrasonic apparatus is shown diagrammatically in FIG. 1 in which an ultrasonic transducer 1 is rotated as shown by the arrow to rotate an ultrasonic beam 2 through a body 3. The return echo signals received by transducer 1, at each position of beam 2, are displayed on a monitor 4 of which the scan is synchronised with transducer 1 such that the display line 5 moves with scanned beam 2. Thus echoes are shown on the display, by brightening the display vector, at a position visually equivalent to their position in body 3. As mentioned before, for one transducer the rotation may be through 360°. No echoes are displayed when the transducer 1 faces away from body 3 and the display is resumed when beam 2 returns to body 3.

To accelerate the procedure two transducers 1a and 1b may be used back to back as shown in FIG. 2. Generally they are switched so that at any time only the transducer 1 facing into body 3 is activated. The scan of monitor 4 is still synchronised so that the display line 5 traces out the beam for the transducer in operation. If the transducers are accurately positioned, echoes from fixed objects appear in the same place for each beam 2.

FIG. 3 shows, to an exaggerated extent, the result of a misalignment of the two transducers. As shown, the beam 2b is displaced by angle $\theta$ from the position which would align with beam 2a. The display on monitor 4 shows the result of the repeated scans for a single reflecting object 6. Beam 2a shows an echo at 7a. Subsequently, a further display scan is initiated, on the assumption that beam 2b is exactly 180° behind beam 2a. However, it is $(180+\theta)°$ behind. Thus the echo 7b from object 6 will be displayed $\theta°$ ahead of its true bearing. For regularly, and quickly repeating displays, the display thus provides a double, or at least blurred image of each reflecting object.

In many transducer probes more than two transducers are used. It will be apparent, however, that the error described is applicable to any number of transducers. Similarly, the solution which will be described for two transducers can readily be extended to larger numbers.

FIG. 4 shows one method of correcting for the error. FIG. 4a shows in solid and chain dotted lines the display vectors and their loci for transducers 1a and 1b respectively, and the two corresponding positions 7a and 7b of the echoes of object 6. As in FIG. 3, the display vectors showing the echo are displaced by angle $\theta$. The error is corrected by retaining the display for transducer 1a from 0° to 180° but shifting the display for transducer 1b to the range from $(0-\theta)°$ to $(180-\theta)°$. The result is shown in FIG. 4b.

There is shown in FIGS. 5a and 5b respectively perspective and part plan views of a typical practical ultrasonic probe head of known type, which can incorporate the invention. In this arrangement the two ultrasonic transducers 1a and 1b are shown although the positions of two further possible transducers 1c and 1d are shown in broken outline. The transducers are mounted on a cylinder 8 arranged to rotate on an axis 9 driven by a belt 10 from a motor 11 via a gear arrangement 12. The system is mounted in a housing 13 with a window 14 of material suitably transmissive to ultrasound, the transducer cylinder 8 being included in suitable ultrasound 'transparent' fluid for coupling purposes.

There is also included a slip ring brush assembly 15 which transfers electrical signals between a transmitter receiver unit (not shown) and the transducers 1. These signals are switched in a transducer switching unit 16 to transfer electrical signals only to the transducer 1 which is in a suitable position to transmit the ultrasound beam 17 into the body being examined and to receive echo signals therefrom.

The transducer switching unit 16 receives switching signals from a sector switching unit 18 which is in turn provided with signals indicating the progress of the rotation of cylinder 8. These latter signals in this example take the form of VCos and Vsin signals from Unit 19 which is a resolver type of position indicator mounted, in this example to rotate about the same axis as motor 11 and driven by the motor through the gear arrangement 12. Cos and sin are used to represent the cosine and sine of the angle of displacement from a suitable origin.

The switching unit 18 resets the signals indicating position and provides an output of VCos and Vsin, for the individual transducer energised at any time, for control of the display unit. It is these signals which have been described hereinbefore as requiring corrections for assembly inaccuracies and it is proposed to rotate the display vector, as described with reference to FIG. 4b, by an angle $\theta°$ by introducing a phase shift of $\theta°$ in the sine and cosine voltages, for the transducer or transducers which are displaced, before applying the signals to the display. It is convenient to include circuits, for applying the corrections, in the unit 18. It will be appreciated, however, that the circuits could be provided independently and that they could be used with moving transducer units different to that described with reference to FIG. 5a and 5b.

Considering the sine and cosine voltages before correction to be $$S = V \sin \omega t$$
$$C = V \cos \omega t$$

then after correction they may be given as S' and C' so that $$S' = V \sin (\theta + \omega t)$$

and $$C' = V \cos (\theta + \omega t)$$

These may be expanded to $$S' = V \sin \theta \cos \omega t + V \cos \theta \sin \omega t$$
$$C' = V \cos \theta \cos \omega t - V \sin \theta \sin \omega t$$

For small angles (say, less than 2.5°) $\cos \theta$ may be taken as 1, with negligible error, and $\sin \theta$ may taken as a small number proportional to $\theta$, say n. S' and C' may then be written $$S' = n V \cos \omega t + V \sin \omega t$$

$$C' = V \cos \omega t - n V \sin \omega t$$

or $$S' = S + nC$$
$$C' = C - nS$$

Correction has been shown for the case explained hereinbefore, it can be shown as a general principle that phase angle may be adjusted in any case by suitable combination of sine with cosine or cosine with sine or both. This is especially suitable for the ultrasonic arrangement described herein, although in certain other cases the consequent changes to the signal amplitudes may preclude use of the technique.

In this example the correction may readily be generated by adding a controlled fraction n of the cosine waveform to the sine waveform and simultaneously subtracting the same fraction n of the sine waveform from the cosine waveform.

There is shown in FIG. 6 a suitable circuit for that purpose. Two amplifiers 20 and 21 are arranged as inverting and summing amplifiers. Potentiometers 22 and 23 are then adjusted to provide the required correction components. Two switches 24 and 25 are provided so that when they are open the circuit operates without correction and when they are closed the correction is applied. The switches have been illustrated as mechanical switches but in practice they may conveniently be electronic switches. The switches are arranged to be open when one transducer (1a) is in use and closed when the other transducer (1b) is in use. The potentiometers setting the correction should be set for the particular transducer probe in use. This may conveniently be achieved by directing the probe at a single known and fixed object in an ultrasound transmitting material. The potentiometers are adjusted until a single echo is displayed.

In a practical transducer probe it is desirable to be able to adjust the potentiometers 22 and 23 simultaneously and from a remote position so that they, or circuits for the same purposes, may be situated within the probe casing or the probe connector. It is also preferable for remote control that the control is effected by signals which would not be adversely affected by filtering the signals to reduce or eliminate the effect of induced interference on the signal leads. In this case control is by a unipolarity voltage.

A circuit is shown in FIG. 7. An oscillator 26 is arranged to produce a triangular voltage waveform. Two matched amplifiers 27 and 28 are arranged as voltage comparators and the triangular waveform is applied to one input of each. The other of amplifier 28 is a reference voltage $V_A$ which is set midway between the positive and negative peaks of the triangular waveform. The output of amplifier 28 is then a square wave with a 1:1 duty cycle. A reference voltage for amplifier 27 is derived from a potentiometer 29 so that the output of 27 is a square wave whose duty cycle may be varied by adjusting the potentiometer.

A logic selection gate 30 causes two electronic switches 31 and 32 to be operated either by the logic output of amplifier 27 or that of amplifier 28 as determined by transducer selection logic circuit 33. The transducer selection logic is arranged in any suitable form, probably responsive to the resolver output, so that amplifier 27 output is effective when one transducer is operative and amplifier 28 output is effective when the other transducer is operative. This selection logic can conveniently be that used to select the outputs of the transducers for display in the known arrangement. The inputs to switch 31 are the S input (called S+) and an S− input which is simply sine (−180°). The S− input can be provided by passing S+ through an inverter. Similarly the inputs to switch 32 are C (called C+) and C− (Cosine (−180°)). The switching frequency, which is the frequency of oscillation of the triangular waveform, is arranged to be high relative to the frequency of the sine and cosine signals. The outputs of switches 31 and 32 are connected to respective low pass filters 34 and 35 to provide outputs S″ and C″.

When comparator 28 is selected, by gate 30, the switches 31 and 32 connect the two inputs alternately to the respective filters for approximately equal periods because of the 1:1 duty cycle. Consequently, the net output of each filter is approximatey zero. When 27 is selected to drive the switches the duty cycle may be varied and as a result the output of filter 34 may be varied continuously from full amplitude S+, through zero, to full amplitude S−. Similarly, the output of 35 varies from C− to C+. The switches are connected so that when 31 connects to S+, 32 connects to C− and vice versa. Thus when S″=S+, C″=C−. If then S″ and C″ are connected to C+ and S+ respectively, phase shifting is achieved according to $$\text{Sin }(\theta+\omega t) = \text{Sin }\omega t + \text{Sin }\theta \text{ Cos }\omega t$$

and $$\text{Cos }(\theta+\omega t) = \text{Cos }\omega t - \text{Sin }\theta \text{ Sin }\omega t$$

which is the same effect as in the FIG. 6 arrangement with switches 24 and 25 closed. Of course, when S″ and C″ are zero, the effect is that of opening switches 24 and 25. Clearly it is not necessary to use such an arrangement, including reference $V_A$ and amplifier 28, to achieve a zero output. However, with the arangement described any drift or change of operating conditions of the whole correction chain, from amplifiers 27, 28 to the output, will affect the different transducers equally. Thus the so-called 'zero' will change with the actual correction and the relative difference between the transducers will remain unchanged. The zero is in practice relative to one of the transducers and not an absolute zero.

The magnitude of Sin $\theta$ is effectively set by potentiometer 29 and as for FIG. 6 may be calibrated for a transducer probe against a known fixed object. It will be apparent from the circuit of FIG. 7, that the circuits prior to and including logic selection gate 30 can be situated remote from the transducer probe head in which the other circuits are included. If desired, only potentiometer 29 may be so situated and its unipolar voltage transmitted to the probe head.

It has been mentioned herein that the sine and cosine signals are provided by resolver 19. It will be understood that such a resolver should preferably be constructed to high tolerances to provide the desired accuracy of output. Such resolvers are expensive and it would be desirable to use cheaper but less accurate resolvers. It will be apparent that errors, due to constructional tolerances, will be substantially constant phase errors for any single resolver, and it is proposed that the phase error corrections described herein are used with appropriate minor modifications to correct the resolver output for phase errors therein. The adaptations required will be obvious to those skilled in the art from the circuits described hereinbefore.

What I claim is:

1. An arrangement for operating on sine and cosine components of a rotating vector signal, representing at different times the positions of different ones of two or more investigative transducers, rotating about an axis with constant relative phase, for control of a display on which the transducer outputs are displayed in alternation, the arrangement including means for varying the relative phase of the vector signal when representing at least one of said transducers to the vector signal when representing a first transducer, to correct display errors resulting from misalignment of said at least one transducer relative to said first transducer.

2. An arrangement according to claim 1 in which the sine and cosine components are provided by an angular resolver cooperating with revolving transducers.

3. An arrangement according to claim 2 further arranged to vary the phase of said vector signal to compensate for errors in said resolver.

4. An arrangement according to claim 1 in which the transducers are ultrasonic transducers.

5. An arrangement for operating on sine and cosine components of a rotating vector signal representing at different times the positions of different ones of two or more investigative transducers, rotating about an axis with constant relative phase, for control of a display on which the transducer outputs are displayed in alternation, the arrangement including means for varying the relative phase of the vector signal when representing at lease one of said transducers to the vector signal when representing a first transducer, to correct display errors resulting from misalignment of said at least one transducer relative to said first transducer in which the means for varying comprises means for combining a proportion of at least one component of the vector signal with the other component.

6. An arrangement according to claim 5 in which the means for varying comprises means for adding a controlled fraction of the cosine component of said vector signal to the sine component and means for subtracting the same fraction of the sine component from the cosine component.

7. An arrangement for operating on sine and cosine components of a rotating vector signal representing at different times the positions of different ones of two or more investigative transducers, rotating about an axis with constant relative phase, for control of a display on which the transducer outputs are displayed in alternation, the arrangement including means for varying the relative phase of the vector signal when representing at least one of said transducers to the vector signal when representing a first transducer, to correct display errors resulting from misalignment of said at least one transducer relative to said first transducer including means for subjecting the sine and cosine components to 180° phase displacement to form sine and minus sine components, means for switching at a controlled rate between the sine and minus sine components to form a phase shifted sine component, means for switching at said controlled rate between the minus cosine and cosine components to form a phase shifted cosine component and means for varying said controlled rate.

8. An ultrasonic examination system including: a probe unit which includes at least two transducers rotating about an axis to alternately scan a body to be examined; means for applying to a common display arrangement the output of the transducer currently scanning the body to display both outputs in alternation; means for providing sine and cosine components of a vector signal, representing the position within its scan of the transducer currently scanning, for control of the display of the respective output; means for modifying at least one component of the vector signal when representing at least one transducer to vary the phase thereof relative to the phase of the vector signal when representing a first transducer so that the alternating displays are maintained in the correct relative phase.

9. An ultrasonic examination system including: a probe unit which includes at least two transducers rotating about an axis to alternately scan a body to be examined; means for applying to a common display arrangement the output of the transducer currently scanning the body to display both outputs in alternation; means for providing sine and cosine components of a vector signal, representing the position within its scan of the transducer currently scanning, for control of the display of the respective output; means for modifying at least one component of the vector signal when representing at least one transducer to vary the phase thereof relative to the phase of the vector signal when representing a first transducer so that the alternating displays are maintained in the correct relative phase wherein the means for modifying includes means for adding, to at least one component, a proportion of the other.

10. A system according to claim 9 in which the means for modifying comprises means for adding a controlled fraction of the cosine component of said vector signal to the sine component and means for subtracting the same fraction of the sine component from the cosine component.

11. An ultrasonic examination system including: a probe unit which includes at least two transducers rotating about an axis to alternately scan a body to be examined; means for applying to a common display arrangement the output of the transducer currently scanning the body to display both outputs in alternation; means for providing sine and cosine components of a vector signal, representing the position within its scan of the transducer currently scanning, for control of the display of the respective output; means for modifying at least one component of the vector signal when representing at least one transducer to vary the phase thereof relative to the phase of the vector signal when representing a first transducer so that the alternating displays are maintained in the correct relative phase; in which the means for modifying includes means for subjecting the sine and cosine components to 180° phase displacement to form minus sine and minus cosine components, means for switching at a controlled rate between the sine and minus sine components to form a phase shifted sine component, means for switching at said controlled rate between the minus cosine and cosine components to form a phase shifted cosine component and means for varying said controlled rate.

12. A method of maintaining the correct relative phase of successive displays, each representing the output of a respective one of two or more ultrasonic transducers substantially at predetermined spacing on a rotating transducer device for scanning a body, where the displays are controlled by sine and cosine components of a vector signal representing the angular position of a transducer currently in operation; the method including modifying at least one component of the vector signal when representing at least one transducer to vary the phase of said vector signal relative to the phase of the vector signal when representing another transducer to correct for departures of the positions of the transducers from said predetermined spacing.

13. A method according to claim 12 wherein the relative phase is adjusted by scanning a well-defined object and varying the modification of said at least one component to provide coincident displays for each of the transducers.

14. A method of maintaining the correct relative phase of successive displays, each representing the output of a respective one of two or more ultrasonic transducers substantially at predetermined spacing on a rotating transducer device for scanning a body, where the displays are controlled by sine and cosine components of a vector signal representing the angular position of a transducer currently in operation; the method including modifying at least one component of the vector signal when representing at least one transducer to vary the phase of said vector signal relative to the phase of the vector signal when representing another transducer to correct for departures of the positions of the transducers from said predetermined spacing and adding, to the at least one component, a proportion of the other component.

15. A method according to claim 14 including the step of subtracting from the other component the same proportion of the at least one component.

16. For an ultrasonic apparatus incorporating: a rotating transducer device having two or more ultrasonic transducers at predetermined spacing thereon to scan a body as the said device rotates; position sensing means providing sine and cosine components of a vector signal representing the position of said device in said rotation; and a display on which are displayed in sequence the outputs of said transducers at timing determined by said vector signal and the predetermined spacing of said transducers, a method of correcting the relative timing of the successive displays to correct for phase errors resulting from deviations of the transducer spacing from its predetermined values, the method including modifying at least one component of the vector signal when the output of at least one transducer is being displayed to vary its phase from the phase difference required for said predetermined spacing relative to its phase when the output of another transducer is being displayed.

17. An ultrasonic examination system including: a rotatable transducer unit; on which at least two ultrasonic transducers are mounted substantially at predetermined spacing to transmit ultrasonic energy, receive reflected ultrasonic energy and provide output signals indicative of the intensity of the reflected energy received; means for rotating said transducer unit to cause said transducers to successively scan a body to be examined; position sensitive means providing sine and cosine components of a vector signal representing the position in said rotation of said transducer unit; a scanning display arrangement arranged to display the output signals derived from said transducers for reflection in said body in sequence, the scanning timing being determined by said sine and cosine components; and correction means for varying the scanning timing for displaying the output of different transducers, to correct for deviations of the transducer spacing from its predetermined values, wherein the correction means comprises means for modifying at least one of said components.

18. An arrangement for operating on sine and cosine components of a rotating vector signal, representing at different times the positions of different ones of two or more angularly spaced investigative transducers rotating about an axis, for control of a display on which the transducer outputs are successively displayed on a scan whose position is determined by said vector signal, the arrangement including means for varying the phase of the vector signal when the output of at least one of said transducers is being displayed, relative to the phase thereof when the output of another of said transducers is being displayed, to align the positions of the scans for the transducers in the presence of errors in the relative positioning thereof.

19. An arrangement according to claim 18 in which the means for varying comprises means for combining a proportion of at least one component of the vector signal with the other component.

20. An ultrasonic examining system including: an ultrasonic transducer unit arranged to be rotatable on an axis; a plurality of ultrasonic transducers mounted on said unit and arranged to transmit ultrasonic energy and receive reflected ultrasonic energy and produce output signals indicative of the received energy; means for rotating the said unit and therewith said transducers about said axis; a position sensitive device for producing sine and cosine components of a vector signal indicative of the positions of said unit in said rotation; a display on which the output signals are displayed at positions determined by said vector signal; and means for modifying the vector signal by combining a proportion of at least one component with the other component to compensate the display for phase errors in said vector signal.

* * * * *